(12) United States Patent
Chava et al.

(10) Patent No.: US 8,791,259 B2
(45) Date of Patent: Jul. 29, 2014

(54) PROCESS FOR THE PREPARATION OF TENOFOVIR

(71) Applicant: Aptuit Laurus Private Limited, Hyderabad (IN)

(72) Inventors: Satyanarayana Chava, Hyderabad (IN); Seeta Ramanjaneyulu Gorantla, Hyderabad (IN); Venkata Sunil Kumar Indukuri, Hyderabad (IN); Sree Rambabu Joga, Hyderabad (IN)

(73) Assignee: Laurus Labs Private Limited, Hyderabad (IN)

( * ) Notice: Subject to any disclaimer, the term of this patent is extended or adjusted under 35 U.S.C. 154(b) by 72 days.

(21) Appl. No.: 13/685,486

(22) Filed: Nov. 26, 2012

(65) Prior Publication Data

US 2013/0165413 A1    Jun. 27, 2013

Related U.S. Application Data

(63) Continuation-in-part of application No. PCT/IN2011/000399, filed on Jun. 14, 2011.

(51) Int. Cl.
| | | |
|---|---|---|
| *C07D 473/00* | (2006.01) | |
| *C07D 473/34* | (2006.01) | |
| *C07C 51/41* | (2006.01) | |
| *C07C 57/15* | (2006.01) | |
| *C07F 9/6561* | (2006.01) | |
| *A61K 31/675* | (2006.01) | |

(52) U.S. Cl.
CPC .......... *C07F 9/65616* (2013.01); *C07D 473/34* (2013.01); *C07C 51/412* (2013.01); *C07C 57/15* (2013.01); *A61K 31/675* (2013.01)
USPC ........................................................ 544/277

(58) Field of Classification Search
None
See application file for complete search history.

(56) References Cited

U.S. PATENT DOCUMENTS

| 5,733,788 A | 3/1998 | Bischofberger |
| 5,922,695 A | 7/1999 | Arimilli et al. |
| 7,390,791 B2 | 6/2008 | Becker et al. |

FOREIGN PATENT DOCUMENTS

| IN | WO2008007392 | * | 1/2008 | ........... C07D 473/34 |
| WO | WO-9403467 A2 | | 2/1994 | |
| WO | WO-2008007392 A2 | | 1/2008 | |

* cited by examiner

*Primary Examiner* — Jeffrey H Murray
(74) *Attorney, Agent, or Firm* — Blank Rome LLP

(57) ABSTRACT

The present invention provides a process for the preparation of tenofovir. The present invention also provides a process for the preparation of tenofovir disoproxil or a salt thereof and its pharmaceutical composition using the tenofovir of the present invention.

18 Claims, 3 Drawing Sheets

PROCESS FOR THE PREPARATION OF TENOFOVIR

PRIORITY

The present application is a continuation-in-part of, and claims the benefit of the filing date of, PCT/IN2011/000399, filed Jun. 14, 2011, which is related to Indian Patent Application No. 3791/CHE/2010, filed May 6, 2011, both of which are related to and claim the benefit of Indian Provisional Application No. 3791/CHE/2010, filed Dec. 13, 2010. The contents of those applications are incorporated by reference herein.

FIELD OF THE INVENTION

The present invention generally relates to a process for the preparation of Tenofovir, a process for its conversion into Tenofovir disoproxil and its pharmaceutically acceptable salts, and pharmaceutical compositions containing the same.

BACKGROUND OF THE INVENTION

Tenofovir, also known as 9-[2-(R)-(phosphonomethoxy)propyl]adenine (PMPA), is represented by the following structure of Formula I:

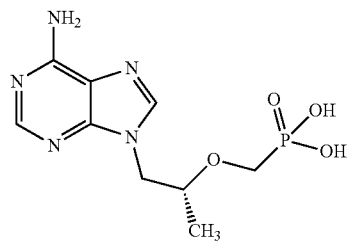

Tenofovir is approved for commercial use as in the form of Tenofovir disoproxil fumaric acid salt, chemically known as 9-[(R)-2-[[bis[[(isopropoxycarbonyl)oxy]methoxy]phosphinyl]methoxy]propyl]adenine fumarate, is represented by the following structure of Formula:

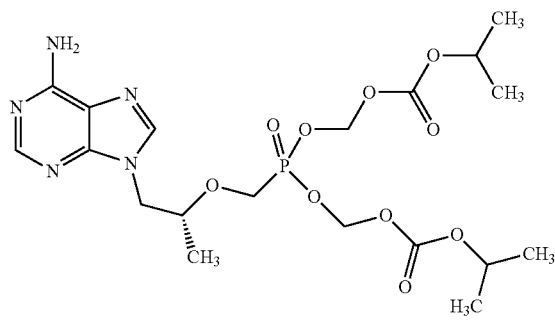

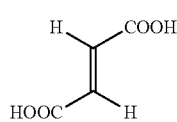

Tenofovir disoproxil fumarate is a highly potent antiviral agent and is available in the market under the brand name VIREAD® in the form of 300 mg of oral tablets and in combination with other antiviral agents.

Patent publication WO 94/03467 ("the '467 publication") discloses a process for preparation of tenofovir by reaction of 9-[2-(R)-hydroxy propyl)-N-benzoyladenine with di(2-propyl)-p-toluenesulfonyloxy methyl phosphonate in presence of a base such as sodium hydride in dimethyl formamide followed by dealkylation with bromotrimethyl silane in acetonitrile.

U.S. Pat. No. 5,733,788 ("the '788 patent") discloses a process for preparation of tenofovir by reaction of 9-[2-(R)-hydroxy propyl)adenine with diethyl-p-toluenesulfonyloxy methyl phosphonate in presence of Lithium hydride in dimethyl formamide followed by dealkylation with bromotrimethyl silane.

U.S. Pat. No. 5,922,695 ("the '695 patent") discloses a process for preparation of tenofovir by reaction of 9-[2-(R)-hydroxy propyl) adenine with diethyl-p-toluenesulfonyloxy methyl phosphonate and Lithium alkoxide base such as Lithium tert-butoxide in Tetrahydrofuran followed by dealkylation with bromotrimethylsilane.

U.S. Pat. No. 7,390,791 ("the '791 patent") discloses a process for preparation of tenofovir by reaction of 9-[2-(R)-hydroxy propyl) adenine with diethyl-p-toluenesulfonyloxy methyl phosphonate in presence of Magnesium alkoxides such as Magnesium isopropoxide and Magnesium tert-butoxide in dimethyl formamide followed by dealkylation with bromotrimethyl silane.

Disadvantages associated with the '467 publication and the '788 patent are, usage of strong base alone such as sodium hydride and lithium hydride results in low conversion of the starting material, which leads to formation of unwanted by products and low product yields.

The '695 patent and the '791 patent discloses the use of highly expensive metal alkoxide bases such as Lithium tert-butoxide, Magnesium isopropoxide and Magnesium tert-butoxide; which in turn result to an increase in the manufacturing cost.

It would be desirable to provide a process for the preparation of tenofovir, which is simple and cost effective; and a process for its use thereof in the preparation of tenofovir disoproxil fumarate in a convenient, cost efficient manner and a commercial scale.

The present invention provides a process for the preparation of tenofovir, which involves use of a base and a metal salt for the conversion of 9-[2-(R)-hydroxy propyl)adenine into tenofovir. The process of the present invention can be practiced on an industrial scale, and also can be carried out without sacrifice of overall yield.

SUMMARY OF THE INVENTION

The present invention encompasses a process for the preparation of tenofovir and its conversion into tenofovir disoproxil or a pharmaceutically acceptable salt thereof with high product yield and quality.

In accordance with one embodiment, the present invention provides a process for preparing tenofovir, comprising:

a) reacting 9-[2-(R)-(hydroxy)propyl]adenine (HPA) of formula III

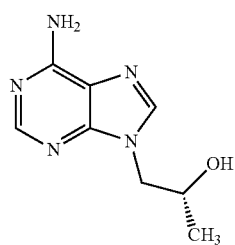

Formula III with di-Alk-p-toluene sulfonyloxy methyl phosphonate in presence of a base and a metal salt in an organic solvent to obtain (R)-9-[2-(di-Alk-phosphono methoxy)propyl]adenine of formula II,

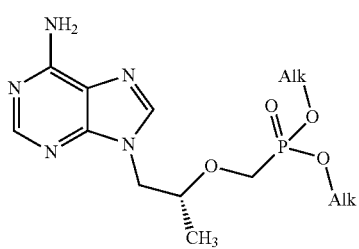

Formula II b) dealkylating the resulting compound of formula II with a suitable dealkylating agent to obtain tenofovir.

In accordance with a second embodiment, the present invention provides a process for preparing tenofovir, comprising:

a) reacting 9-[2-(R)-(hydroxy)propyl]adenine (HPA) of formula III with di-Alk-p-toluene sulfonyloxy methyl phosphonate in presence of a base and a metal salt in an organic solvent to obtain (R)-9-[2-(di-Alk-phosphono methoxy)propyl]adenine of formula II,
wherein the "Alk" represents $C_{1-4}$ alkyl; wherein the base is selected from the group consisting of alkali metal hydroxides, alkali metal hydrides, amide bases, alkali metal alkoxides and alkyl lithium compounds; wherein the metal salt is represented by the formula $MX_2$, wherein the 'M' represents a divalent metal cation selected from zinc, beryllium, magnesium, calcium, strontium and barium; 'X' represents halide, acetate or trifluoromethane sulfonate; wherein the organic solvent is selected from the group consisting of amides, ethers, aromatic hydrocarbons and nitriles;

b) dealkylating the resulting compound of formula II with a suitable dealkylating agent to obtain tenofovir; wherein the dealkylating agent is selected from trialkyl silyl halides such as chloro trimethyl silane, bromotrimethyl silane and iodo trimethyl silane and the like; hydrobromic acid and methane sulfonic acid.

In accordance with a third embodiment, the present invention provides a process for preparing tenofovir, comprising:

a) reacting 9-[2-(R)-(hydroxy)propyl]adenine (HPA) of formula III with di-Alk-p-toluene sulfonyloxy methyl phosphonate in presence of an alkyl metal complex of formula $R^1$-MX in an organic solvent to obtain (R)-9-[2-(di-Alk-phosphono methoxy)propyl]adenine of formula II,
wherein the "Alk" represents $C_{1-4}$ alkyl; '$R^1$' represents $C_{1-8}$ chain or branched alkyl; 'M' represents a divalent metal cation selected from beryllium, magnesium, calcium, strontium and barium; and 'X' represents halide, acetate, or trifluoromethane sulfonate; wherein the organic solvent is selected from the group consisting of amides, ethers, aromatic hydrocarbons and nitriles.

b) dealkylating the resulting compound of formula II with a suitable dealkylating agent to obtain tenofovir; wherein the dealkylating agent is selected from trialkyl silyl halides such as chloro trimethyl silane, bromotrimethyl silane and iodo trimethyl silane and the like; hydrobromic acid and methane sulfonic acid.

In accordance with a fourth embodiment, the present invention provides tenofovir in solid form characterized by an X-ray powder diffraction pattern (XRPD) substantially in accordance with FIG. 1.

In accordance with a fifth embodiment, the present invention provides a process for preparing tenofovir disoproxil or a pharmaceutically acceptable salt thereof, comprising:

a) reacting 9-[2-(R)-(hydroxy)propyl]adenine (HPA) of formula III with di-Alk-p-toluene sulfonyloxy methyl phosphonate in presence of a base and a metal salt in an organic solvent to obtain (R)-9-[2-(di-Alk-phosphono methoxy)propyl]adenine of formula II, b) dealkylating the resulting compound of formula II with a suitable dealkylating agent to obtain tenofovir, c) converting the tenofovir into tenofovir disoproxil ester or a pharmaceutically acceptable salt thereof.

In accordance with a sixth embodiment, the present invention provides a process for preparing tenofovir disoproxil or a pharmaceutically acceptable salt thereof, comprising:

a) reacting 9-[2-(R)-(hydroxy)propyl]adenine (HPA) of formula III with di-Alk-p-toluene sulfonyloxy methyl phosphonate in presence of a base and a metal salt in an organic solvent to obtain (R)-9-[2-(di-Alk-phosphono methoxy)propyl]adenine of formula II,
wherein the "Alk" represents $C_{1-4}$ alkyl; wherein the base is selected from the group consisting of alkali metal hydroxides, alkali metal hydrides, amide bases, alkali metal alkoxides and alkyl lithium compounds; wherein the metal salt is represented by the formula $MX_2$, wherein the 'M' represents a divalent metal cation selected from zinc, beryllium, magnesium, calcium, strontium and barium; 'X' represents halide, acetate or trifluoromethane sulfonate; wherein the organic solvent is selected from the group consisting of amides, ethers, aromatic hydrocarbons and nitriles;

b) dealkylating the resulting compound of formula II with a suitable dealkylating agent to obtain tenofovir; wherein the dealkylating agent is selected from trialkyl silyl halides such as chloro trimethyl silane, bromotrimethyl silane and iodo trimethyl silane and the like; hydrobromic acid and methane sulfonic acid;

converting the tenofovir into tenofovir disoproxil ester or a pharmaceutically acceptable salt thereof.

In accordance with a seventh embodiment, the present invention provides a process for preparing tenofovir disoproxil or a pharmaceutically acceptable salt thereof, comprising:

a) reacting 9-[2-(R)-(hydroxy)propyl]adenine (HPA) of formula III with di-Alk-p-toluene sulfonyloxy methyl phosphonate in presence of an alkyl metal complex of formula $R^1$-MX in an organic solvent to obtain (R)-9-[2-(di-Alk-phosphono methoxy)propyl]adenine of formula II, b) dealkylating the resulting compound of formula II with a suitable dealkylating agent to obtain tenofovir, c) converting the tenofovir into tenofovir disoproxil ester or a pharmaceutically acceptable salt thereof,
wherein the "Alk" represents $C_{1-4}$ alkyl; '$R^1$' represents $C_{1-8}$ chain or branched chain alkyl; 'M' represents a divalent metal cation selected from beryllium, magnesium, calcium, strontium and barium; 'X' represents halide, acetate, or trifluoromethane sulfonate; wherein the dealkylating agent is selected from trialkyl silyl halides such as chloro trimethyl silane, bromotrimethyl silane and iodo trimethyl silane and the like; hydrobromic acid and methane sulfonic acid; and an organic solvent is selected from the group consisting of amides, ethers, aromatic hydrocarbons and nitriles.

In accordance with an eighth embodiment, the present invention provides Tenofovir disoproxil fumarate substantially free of 9-[2-(R)-(hydroxy)propyl]adenine (HPA) of formula III.

In accordance with a ninth embodiment, the present invention provides a pharmaceutical composition comprising a therapeutically effective amount of tenofovir disoproxil or a pharmaceutically acceptable salt thereof prepared by the processes of the present invention and at least one pharmaceutically acceptable carrier.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE INVENTION

Figure 1:
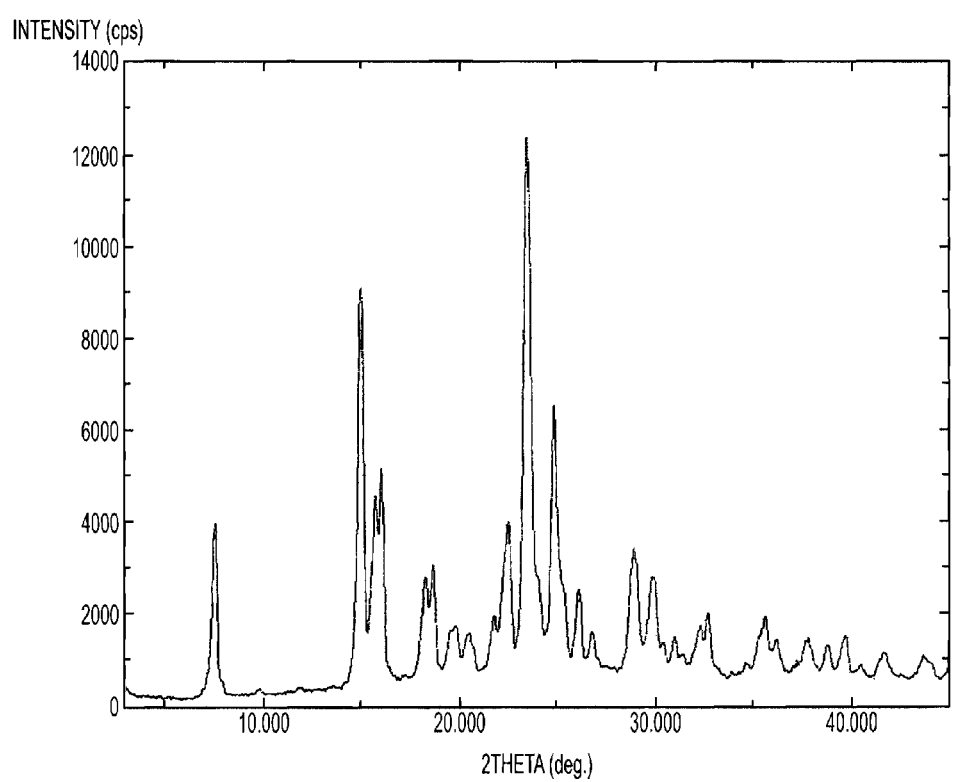
FIG. 1 is the characteristic powder X-ray diffraction pattern (XRPD) of tenofovir.

The present invention provides an improved process for the preparation of tenofovir. In particular, the present invention provides a process to prepare tenofovir by using a base and a metal salt in the conversion of 9-[2-(R)-(hydroxy)propyl]adenine (HPA) in to tenofovir. The present invention further provides a process for preparing tenofovir disoproxil or a pharmaceutically acceptable salt thereof from the tenofovir obtained from the process of the present invention.

In one embodiment, the present invention provides a process for preparing tenofovir, comprising:

a) reacting 9-[2-(R)-(hydroxy)propyl]adenine (HPA) of formula III

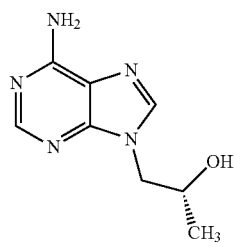

Formula III with di-Alk-p-toluene sulfonyloxy methyl phosphonate in presence of a base and a metal salt in an organic solvent to obtain (R)-9-[2-(di-Alk-phosphono methoxy)propyl]adenine of formula II,

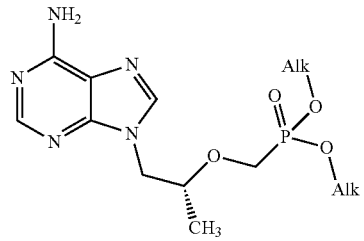

Formula II wherein "Alk" represents $C_{1-4}$ alkyl, preferably ethyl;

b) dealkylating the resulting compound of formula II with a suitable dealkylating agent to obtain tenofovir.

The starting material 9-[2-(R)-(hydroxy)propyl]adenine (HPA) of formula III is known in the art and can be prepared by any known method, for example starting compound of formula III may be synthesized as disclosed in U.S. Pat. No. 5,922,695.

The base in the foregoing process may be selected from the group consisting of alkali metal hydroxides, alkali metal hydrides, amide bases, alkali metal alkoxides, alkali metal carbonates, alkyl lithium compounds, alkaline earth metal alkoxides and amines. The alkali metal hydroxides include, but are not limited to sodium hydroxide, lithium hydroxide, potassium hydroxide, cesium hydroxide and the like; alkali metal hydrides include, but are not limited to sodium hydride, potassium hydride, lithium hydride and the like; amide bases include, but are not limited to alkali metal amides such as lithium amide, sodium amide, potassium amide, cesium amide, rubidium amide and the like; alkyl substituted metal silyl amides such as lithium hexamethyl disilazane (LiHMDS), sodium hexamethyl disilazane (NaHMDS), potassium hexamethyl disilazane (KHMDS) and the like; alkali metal alkyl amides such as sodium methyl amide, sodium dimethyl amide, potassium methyl amide, potassium dimethyl amide, sodium ethyl amide, sodium diethyl amide, potassium ethyl amide, potassium diethyl amide, n-butyl lithium amide and the like; and alkaline earth metal amides such as beryllium amide, magnesium amide, calcium amide, strontium amide, barium amide and the like; alkali metal alkoxides include, but are not limited to methoxides of lithium, sodium, and potassium; ethoxides of lithium, sodium, and potassium, tertiary butoxides of lithium, sodium, and potassium; alkali metal carbonates include, but are not limited to sodium carbonate, lithium carbonate, potassium carbonate, cesium carbonate and the like; alkyl lithium compounds include, but are not limited to $C_{1-6}$ alkyl lithium such as methyl, ethyl, n-propyl, isopropyl, n-butyl, isobutyl, secondary butyl, tertiary butyl, pentyl, isopentyl, n-hexyl and the like; alkaline earth metal alkoxides include, but are not limited to magnesium methoxide, magnesium ethoxide, magnesium isopropoxide, magnesium tertiary butoxide and the like; and amines include, but are not limited to dimethyl amine, trimethyl amine, triethyl amine, diisopropyl amine, diisopropyl ethyl amine, piperidine, morpholine, N-methyl morpholine, pyridine, 1,8-diazabicycloundec-7-ene (DBU), 1,4-diazabicyclo[2.2.2]octane (DABCO) and the like. Preferably the base is selected from the group consisting of sodium hydride, lithium hydride, sodium amide, potassium amide, sodium dimethyl amide, magnesium isopropoxide, magnesium tertiary butoxide, lithium tertiary butoxide; more preferably sodium hydride, lithium hydride or sodium amide.

The metal salt in the foregoing process may be represented by the following formula $MX_2$, wherein the 'M' represents a divalent metal cation selected from the group consisting of zinc, beryllium, magnesium, calcium, strontium and barium, preferably magnesium; 'X' represents halide, acetate, sulfate, bisulfate, carbonate, bicarbonate or trifluoromethane sulfonate. The halide includes, but is not limited to fluoro, bromo, chloro, iodo and the like. Preferably, the metal salt is selected from the group consisting of magnesium chloride, magnesium acetate, magnesium sulfate, magnesium bisulfate, magnesium carbonate, magnesium bicarbonate or magnesium trifluoromethane sulfonate, zinc chloride; more preferably magnesium chloride or magnesium acetate.

The organic solvent includes, but is not limited to amides, ethers, aromatic hydrocarbons, and nitriles and the like and mixtures thereof. The amides include, but are not limited to dimethyl formamide, dimethyl acetamide, dimethyl sulfoxide, N-methyl pyrrolidinone, hexamethyl phosphoramide and the like and mixtures thereof; ethers include, but are not limited to dimethyl ether, diethyl ether, methyl ethyl ether, diisopropyl ether, methyl tertiary butyl ether, tetrahydrofuran, 1,4-dioxane and the like and mixtures thereof; aromatic hydrocarbons include, but are not limited to toluene, xylenes such as o-, p-, and m-xylene, anisole and the like and mixtures thereof; nitriles include, but are not limited to acetonitrile, propionitrile and the like and mixtures thereof. Preferably the organic solvent is selected from dimethyl formamide, dimethyl acetamide, dimethyl sulfoxide, toluene, tetrahydrofuran, diisopropyl ether, methyl ethyl ether, methyl tertiary butyl ether and mixtures thereof, more preferably dimethyl formamide, toluene or mixtures thereof.

The di-Alk-p-toluene sulfonyloxy methyl phosphonate is di-$C_{1-4}$ alkyl p-toluene sulfonyloxy methyl phosphonate, wherein the $C_{1-4}$ alkyl represents methyl, ethyl, propyl, butyl, isopropyl, isobutyl, and the like; preferably diethyl p-toluene sulfonyloxy methyl phosphonate and can range from about 1 to about 3 mole equivalents per mole of starting HPA, preferably about 1.5 mole equivalents per mole of starting HPA.

The reaction temperature should be sufficient to effect conversion of HPA to tenofovir. Typically the reaction temperature may be from about ambient temperature to about reflux temperature. Preferably the reaction temperature is about 40° C. to about 100° C., more preferably at about 70° C. to about 85° C. The reaction may take from about 2 hours to about 10 hours depending upon the base, metal salt, solvent and temperature chosen, preferably about 4 hours.

The resultant organic layer containing (R)-9-[2-(diethylphosphono methoxy)propyl]adenine of formula II can be further processed directly in the same reaction vessel to form tenofovir of Formula I. Alternatively, the solvent from the organic layer may be concentrated under vacuum to get the residue by any method known in the art, at the end of the reaction and followed by optional crystallization in to solid compound. The step of concentration may be for example distillation, evaporation, rotational drying (such as with the Buchi Rotavapor), freeze drying, fluidized bed drying, flash drying, spin flash drying, and the like, preferably distillation under vacuum.

Step b) of foregoing process may be carried out by adding sufficient amount of dealkylating agent to the resultant product in order to dealkylizing the alkyl groups from the (R)-9-[2-(diethylphosphono methoxy)propyl]adenine of formula II.

The dealkylating agent for use in the dealkylation process may be selected from the group consisting of trialkyl silyl halides such as chloro trimethyl silane, bromotrimethyl silane and iodo trimethyl silane and the like; hydrobromic acid and methane sulfonic acid; preferably dealkylating agent is hydrobromic acid.

The reaction temperature should be sufficient to effect dealkylation. Typically the reaction temperature may be from about ambient temperature to about reflux temperature. Preferably the reaction temperature is about 65° C. to about 110° C., more preferably at about 85° C. to about 100° C. The reaction may take from about 2 hours to about 10 hours depending upon the solvent, acid and temperature chosen. For instance, a reaction carried out at temperature at 90° C. to 95° C., is completed about 4 hours.

After completion of the dealkylation reaction, the resultant reaction mass can be cooled to ambient temperature, after removal of the solid bi-product salts that is produced, such as by filtration, the filtrate can be separated and washed with water immiscible organic solvent. The water immiscible organic solvent includes, but are not limited to ethers such as diethyl ether, isopropyl ether, methyl tertiary butyl ether and the like and mixtures thereof; chlorinated hydrocarbons such as methylene chloride, ethylene chloride, chloroform and the like and mixtures thereof; aromatic hydrocarbons include, but are not limited to toluene, xylenes such as o-, p-, and m-xylene and the like and mixtures thereof; preferably the water immiscible organic solvent is methylene chloride, methyl tertiary butyl ether and toluene, more preferably methylene chloride. After separating the water immiscible organic solvent from the aqueous layer, the resultant water containing the target product may be separated by adjusting the pH of the reaction to about 2 to about 4, preferably about 2 to about 3.

The adjustment of pH may be carried out with bases, wherein the bases are known in the art, for example sodium hydroxide, potassium hydroxide and the like, preferably the base is sodium hydroxide.

The resultant tenofovir can be isolated by solvent crystallization, solvent precipitation and the like. The tenofovir can be recovered by any conventional technique known in the art, for example filtration. Typically, if stirring is involved, the temperature during stirring can range from about −10° C. to about +20° C., preferably at about −10° C. to about +10° C., more preferably at temperature between about 0° C. to about 5° C.

The resultant tenofovir product may optionally slurred or crystallized with water. Slurry or crystallization can be suitably carried out at temperature of about 75° C. to about 100° C., preferably at about 95° C. to about 100° C.

The resultant tenofovir can be isolated by cooling the temperature to about 25° C. to about 30° C. The tenofovir can be recovered by any conventional technique known in the art, for example filtration. Typically, if stirring is involved, the temperature during stirring can range from about −10° C. to about +20° C., preferably at about −10° C. to about +10° C., more preferably at temperature between about 0° C. to about 5° C.

The resultant product may optionally be further dried. Drying can be suitably carried out in a tray dryer, vacuum oven, air oven, fluidized bed drier, spin flash dryer, flash dryer and the like. The drying can be carried out at a temperature ranging from about 60° C. to about 90° C. The drying can be carried out for any desired time until the required product purity is achieved, e.g., a time period ranging from about 1 hour to about 20 hours. A high purity level of the resulting tenofovir, obtained by the aforementioned process, may have a chemical purity of at least about 97%, as measured by HPLC, preferably at least about 98%, as measured by HPLC and more preferably at least about 99%, as measured by HPLC.

The tenofovir recovered using the process of the present invention is having substantially free of 9-[2-(R)-(hydroxy)propyl]adenine (HPA) of formula III.

The present invention further provides a process for preparing tenofovir, comprising:

a) reacting 9-[2-(R)-(hydroxy)propyl]adenine (HPA) of formula III with di-Alk-p-toluene sulfonyloxy methyl phosphonate in presence of an alkyl metal complex of formula $R^1$-MX in an organic solvent to obtain (R)-9-[2-(di-Alk-phosphono methoxy)propyl]adenine of formula II, wherein "Alk" represents $C_{1-4}$ alkyl, preferably ethyl, b) dealkylating the resulting compound of formula II with a suitable dealkylating agent to obtain tenofovir.

Wherein '$R^1$' represents a $C_{1-8}$ chain or branched alkyl such as methyl, ethyl, propyl, n-butyl, t-butyl, pentyl, hexyl and the like; 'M' represents a divalent metal cation selected from beryllium, magnesium, calcium, strontium and barium; and 'X' represents halide, acetate, or trifluoromethane sulfonate. The halide includes, but is not limited to fluoro, bromo, chloro, iodo and the like. Preferably, the alkyl metal complex is alkyl magnesium halide, more preferably n-butyl magnesium chloride.

The organic solvent includes, but is not limited to amides, ethers, aromatic hydrocarbons, and nitriles and the like and mixtures thereof. The amides include, but are not limited to dimethyl formamide, dimethyl acetamide, dimethyl sulfoxide, N-methyl pyrrolidinone, hexamethyl phosphoramide and the like and mixtures thereof; ethers include, but are not limited to dimethyl ether, diethyl ether, methyl ethyl ether, diisopropyl ether, methyl tertiary butyl ether, tetrahydrofuran, 1,4-dioxane and the like and mixtures thereof; aromatic hydrocarbons include, but are not limited to toluene, xylenes such as o-, p-, and m-xylene, anisole and the like and mixtures thereof; nitriles include, but are not limited to acetonitrile, propionitrile and the like and mixtures thereof. Preferably the organic solvent is selected from dimethyl formamide, dimethyl acetamide, dimethyl sulfoxide, toluene, tetrahydrofuran, diisopropyl ether, methyl ethyl ether, methyl tertiary butyl ether and mixtures thereof, more preferably tetrahydrofuran.

The di-Alk-p-toluene sulfonyloxy methyl phosphonate is di-$C_{1-4}$ alkyl p-toluene sulfonyloxy methyl phosphonate, wherein the $C_{1-4}$ alkyl represents methyl, ethyl, propyl, butyl, isopropyl, isobutyl, and the like; preferably diethyl p-toluene sulfonyloxy methyl phosphonate and can range from about 1 to about 3 mole equivalents per mole of starting HPA, preferably about 1.5 mole equivalents per mole of starting HPA.

The reaction temperature should be sufficient to effect conversion of HPA to tenofovir. Typically the reaction temperature may be from about ambient temperature to about reflux temperature. Preferably the reaction temperature is about 45° C. to about 85° C., more preferably at about 60° C. to about 70° C. The reaction may take from about 2 hours to about 10 hours depending upon the catalyst, solvent and temperature chosen. For instance, a reaction carried out with n-butyl magnesium chloride at temperature 60° C. to 65° C., is completed about 4 hours.

The resultant organic layer containing (R)-9-[2-(diethylphosphono methoxy)propyl]adenine of formula II can be further processed directly in the same reaction vessel to form tenofovir of Formula I. Alternatively, the solvent from the organic layer may be concentrated under vacuum to get the residue by any method known in the art, at the end of the reaction and followed by optional crystallization in to solid compound. The step of concentration may be for example distillation, evaporation, rotational drying (such as with the Buchi Rotavapor), freeze drying, fluidized bed drying, flash drying, spin flash drying, and the like, preferably distillation under vacuum.

The (R)-9-[2-(diethylphosphono methoxy)propyl]adenine (a compound of Formula II) thus obtained is converted into tenofovir (a compound of Formula I) by dealkylation process as described above.

The present invention encompasses methods of preparing tenofovir and a pharmaceutically acceptable ester, or a salt thereof with high purity. The processes of the invention allow for economical synthesis, shorter reaction times, and yields of high purity.

The present invention provides pharmaceutically acceptable esters, or salts of tenofovir, obtained by a process comprising providing a tenofovir as obtained by the process described above, as a starting material or as an intermediate, where the yield and the purity of the pharmaceutically acceptable esters, or a salt thereof, preferably tenofovir disoproxil fumarate salt may have a purity equal to or greater than about 99.5% as determined by HPLC.

The present invention further provides a process for a preparation of pharmaceutically acceptable esters, or a salt of tenofovir, preferably tenofovir disoproxil or a salt thereof such as fumarate, phosphate, ferulate, caffeic acid salt, p-coumaric acid salt, sinapic acid salt and the like; more preferably tenofovir disoproxil fumarate salt comprising:

a) providing a tenofovir obtained by the processes described above dissolved in one or more organic solvents, and a base;

b) heating the reaction mixture to about 40° C. to about 70° C., preferably at about 50° C. to about 55° C.;

c) treating the resultant reaction mixture with chloromethyl isopropyl carboante to obtain tenofovir disoproxil;

d) saltification of the resultant tenofovir disoproxil into tenofovir disoproxil fumarate;

wherein the one or more organic solvent in step a) include, but are not limited to amides such as dimethyl formamide, dimethyl acetamide, dimethyl sulfoxide, N-methyl pyrrolidinone and the like and mixtures thereof; hydrocarbons such as cyclohexane, toluene, xylene, and the like and mixtures thereof; and the base include, but is not limited to sodium hydroxide, potassium hydroxide, sodium carbonate, potassium carbonate, triethylamine and the like and mixtures thereof. Preferably the organic solvent is N-methyl pyrrolidinone and the base is triethylamine.

Step (c) of the reaction of chloromethyl isopropyl carboante with tenofovir obtained by the processes described above may be carried out at temperature of about 40° C. to about 70° C. The reaction may take from about 2 hours to about 10 hours depending upon the solvent, base and temperature chosen. For instance, a reaction carried out with N-methyl pyrrolidinone, triethylamine base at temperature 50° C. to 55° C., is completed about 3 hours.

After completion of the reaction, the resultant reaction mass can be cooled to ambient temperature, after removal of the solid bi-product salts that is produced, such as by filtration, the organic layer of the filtrate can be separated and washed with water. After separating the water from the tenofovir disoproxil product containing organic layer, the target product may be separated by adding additional water to the organic layer and adjusting the pH of the reaction to about 6 to about 8, preferably about 6.5 to about 7.5 with a base such as aqueous ammonia and separating the product containing organic layer and evaporated completely under vacuum.

Step (d) of the saltification process may be carried out by mixing tenofovir disoproxil obtained by the process as described above with fumaric acid in one or more organic solvents. One or more organic solvent include but are not limited to $C_{1-4}$ alcohol such as methanol, ethanol, n-propanol, isopropanol, n-butanol, isobutanol and the like and mixtures thereof; esters such as methyl acetate, ethyl acetate, isopropyl acetate and the like and mixtures thereof. Preferably the one or more organic solvent selected from methanol, isopropanol, ethyl acetate, more preferably isopropanol.

The fumaric acid can range from about 0.8 to about 2 mole equivalents per mole of starting tenofovir disoproxil, preferably about 1.0 to about 1.5 moles. The fumaric acid can be added either as a solution in organic solvent or it may be added as a solid to the solution of tenofovir disoproxil in an organic solvent. The sequence of addition of fumaric acid is not particularly critical. Additionally, the fumaric acid salt formation can be carried out in any known manner, for example, the fumaric acid can be added into tenofovir disoproxil solution or tenofovir disoproxil solution may be added to the fumaric acid.

Optionally, heating the solution to dissolve the tenofovir disoproxil, typically, the solution is heated at a temperature of at least about 45° C. to about 65° C. Preferably, the solution is heated at about 50° C. to about 55° C. The reaction solution may be cooled at a temperature from about 20° C. or less such that the tenofovir disoproxil fumarate can be isolated by conventional techniques.

In another aspect of the present invention, tenofovir disoproxil fumarate thus obtained may be further purified by slurring the tenofovir disoproxil fumarate in an ester solvent such as methyl acetate, ethyl acetate, isopropyl acetate, and the like and mixtures thereof, with ethyl acetate being preferred.

The present invention provides a tenofovir disoproxil fumarate, obtained by the process described herein, having a purity of at least about 97%, as measured by HPLC, preferably at least about 98% as measured by HPLC, and more preferably at least about 99.5%, as measured by HPLC; and substantially free of 9-[2-(R)-(hydroxy)propyl]adenine (HPA) of formula III, wherein the word "substantially free" refers to tenofovir disoproxil fumarate having less than about 0.15% of formula III, as measured by HPLC, more preferably less than about 0.1% of formula III, as measured by HPLC, still more preferably less than about 0.05% of formula III, as measured by HPLC.

The '467 publication and the '788 patent discloses process for the preparation of tenofovir, which was involved sodium hydride or lithium hydride as base during the reaction of 9-[2-(R)-hydroxy propyl) adenine (HPA) with diethyl-p-toluenesulfonyloxy methyl phosphonate, results tenofovir contain high levels of unconverted 9-[2-(R)-hydroxy propyl) adenine. In contrast, the process herein described arrives at a tenofovir, which may be involved a metal salt along with a base to improve the rate of the reaction. Particularly, the process herein described allows that a tenofovir may be prepared substantially lower level of HPA.

A comparative preparation of tenofovir using a process in the presence of sodium hydride or lithium hydride as described in other processes, yielded a tenofovir that had lower conversion of the HPA and contain high level of N-alkyl tenofovir of the Formula IV than the present process. The results are summarized in Table I, as shown below under example 6 where values are reported as weight percent (wt/wt %) as determined by HPLC.

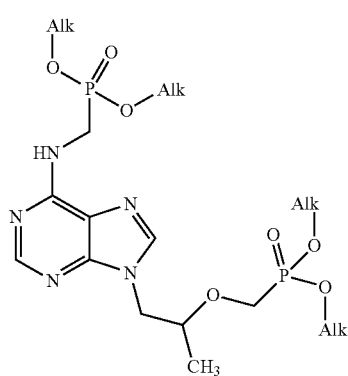

Formula IV wherein the "Alk" represents methyl, ethyl, propyl, butyl, isopropyl or isobutyl.

In one preferred embodiment of the present invention, tenofovir, or its ester or a salt thereof is prepared according to Scheme I:

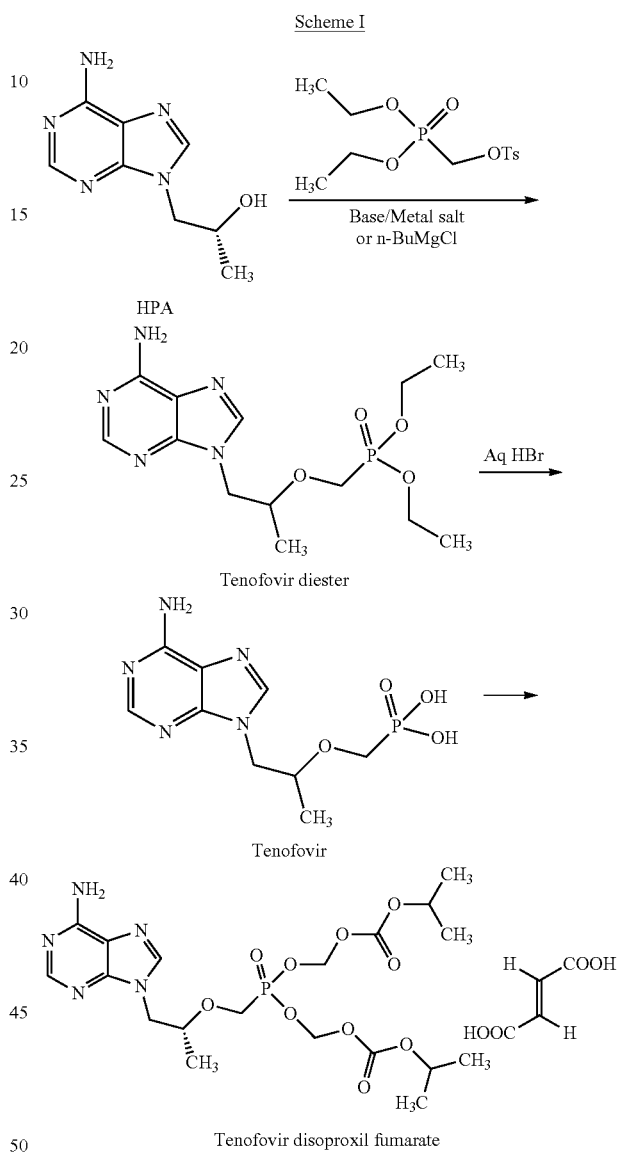

The present invention further provides tenofovir disoproxil or a pharmaceutically acceptable salt, preferably tenofovir disoproxil fumarate obtained by the process described herein, having relatively low content of one or more organic volatile impurities.

The present invention provides a tenofovir disoproxil or a pharmaceutically acceptable salt thereof; preferably the fumarate salt obtained using the process described herein, may have a residual solvent content that is within the limits given by the International Conference on Harmonization of Technical Requirements for Registration of Pharmaceuticals for Human Use ("ICH") guidelines. The guideline solvent level depends on the type of solvent but is not more than about 5000 ppm, or about 4000 ppm, or about 3000 ppm.

The present invention provides a tenofovir disoproxil fumarate, obtained by the process disclosed herein, having less than about 800 parts per million (ppm) $C_{1-4}$ alcohols such as methanol, ethanol, isopropanol, preferably less than about 500 ppm; less than about 500 ppm acetone, preferably less than about 200 ppm; less than about 500 ppm ethyl acetate, preferably less than about 200 ppm; less than about 500 ppm toluene, preferably less than about 200 ppm; less than about 500 ppm cyclohexane, preferably less than about 200 ppm; less than about 500 ppm tetrahydrofuran, preferably less than about 200 ppm; less than about 500 ppm dichloromethane, preferably less than about 100 ppm; less than about 500 ppm dimethyl formamide, preferably less than about 200 ppm; less than about 200 ppm triethyl amine, preferably less than about 10 ppm; less than about 500 ppm N-methyl pyrrolidinone, preferably less than about 100 ppm. The present invention further provides tenofovir disoproxil fumarate, obtained by the process disclosed herein, having less than about 5 ppm acetone; less than about 100 ppm isopropanol; less than about 3 ppm ethyl acetate; less than about 16 ppm dichloromethane; less than about 1 ppm cyclohexane; less than about 3 ppm toluene; less than about 40 ppm dimethyl formamide; less than about 92 ppm N-methyl pyrrolidinone; and less than about 16 ppm triethyl amine.

The present invention provides a tenofovir or its ester or salts thereof, obtained by the above process, as analyzed using the high performance liquid chromatography ("HPLC") with the conditions described below:

Column: Sunfire C18, (250×4.6) mm, 5 μm
Column temperature: 45° C.
Diluent: Water and Methanol (1:1) v/v
Flow rate: 0.8 mL/min
Detection wavelength: UV260 nm
Injection volume: 10 μL
Sample concentration: 0.5 mg/ml
Mobile Phase:
A) Add 1 ml of triethylamine and 1.56 g of sodium dihydrogen phosphate dihydrate in 1000 ml of water. Adjust pH to 5.5 with o-phosphoric acid.
B) Methanol
Gradient Program

| Time (Min) | Mobile phase A % (v/v) | Mobile phase B % (v/v) |
|---|---|---|
| 0 | 85 | 15 |
| 15 | 50 | 50 |
| 25 | 30 | 70 |
| 30 | 30 | 70 |
| 35 | 85 | 15 |
| 40 | 85 | 15 |

The present invention provides a tenofovir or its ester or salts thereof, obtained by the above process, as analyzed using the X-Ray powder diffraction with the conditions described as follows: an X-ray powder Diffractometer equipped with a Cu-anode ($[\lambda]=1.54$ Angstrom), X-ray source operated at 30 kV, 15 mA and a Ni filter is used to strip K-beta radiation. Two-theta calibration is performed using an NIST SRM 640c Si standard. The sample was analyzed using the following instrument parameters: measuring range=3-45°2θ; step width=0.020°; and scan speed=2°/minute.

The present invention provides a tenofovir or its ester or salts thereof, obtained by the above process, as analyzed using the differential scanning calorimetry (DSC) with the conditions described as follows: a Differential Scanning calorimeter (DSC Q200, TA instrumentation, Waters) at a scan rate of 2° C. per minute with an Indium standard.

Another aspect of the present invention is directed to a pharmaceutical composition containing at least the substantially pure tenofovir disoproxil fumarate disclosed herein and at least one pharmaceutically acceptable excipient. Such pharmaceutical composition may be administered to a mammalian patient in any dosage form, e.g., liquid, powder, elixir, injectable solution, etc.

In one embodiment, the tenofovir disoproxil fumarate disclosed herein for use in the pharmaceutical compositions of the present invention can have a $D_{50}$ and $D_{90}$ particle size of less than about 400 microns, preferably less than about 200 microns, more preferably less than about 150 microns, still more preferably less than about 50 microns and most preferably less than about 15 microns. The particle sizes of the tenofovir disoproxil fumarate prepared according to the present invention can be obtained by any milling, grinding, micronizing, or other particle size reduction method known in the art to bring the solid state tenofovir disoproxil fumarate into any of the desired particle size range.

The following examples are provided to enable one skilled in the art to practice the invention and are merely illustrative of the invention. The examples should not be read as limiting the scope of the invention as defined in the claims.

Example 1

Preparation of Tenofovir (Using Sodium Amide and Magnesium Chloride)

To a clean 3-necked 2 L round bottom flask equipped with a mechanical stirrer, thermometer socket and addition funnel was charged dimethyl formamide (400 ml) and 9-[2-(R)-(hydroxy)propyl]adenine (HPA) of formula III (100 gms) at temperature 20° C. to 35° C. Cooled to 0° C. to 5° C. and added sodium amide (40.4 gms) at temperature 0° C. to −10° C. and stirred for 30 minutes at same temperature. Heated to 25° C. to 30° C. and stirred for 2 hours at same temperature. Added magnesium chloride (49.2 gms) and stirred for 1 hour at 25° C. to 30° C. To the reaction mass was charged toluene (300 ml) and heated to 50° C. to 55° C. and stirred for 4 hours at same temperature and then again heated to 75° C. to 80° C. At this temperature added diethyl p-toluene sulfonyloxy methyl phosphonate (250 gms) (DESMP) and stirred for 4 hours at same temperature. Reaction was monitored by HPLC and observed 78% of the reaction product formed. The solvent was removed from the reaction mixture by distillation under vacuum at below 70° C. to obtain (R)-9-[2-(diethylphosphono methoxy)propyl]adenine of formula II as thick residue. Cooled the resultant residue to 25° C. to 35° C. and charged aqueous hydrobromic acid (650 ml). Heated to 90° C. to 95° C. and stirred for 2 hours at same temperature. After completion of the reaction, the reaction mass was cooled to 25° C. to 30° C. and stirred for 30 minutes at same temperature. Filtered the salts formed and washed the salts with methylene chloride (300 ml). Taken filtrate and separated methylene chloride layer from the aqueous layer and then adjusted the aqueous layer pH to 2.5 to 3 with 50% sodium hydroxide solution at 20° C. to 30° C. Stirred the solution for 1 hour at 20° C. to 25° C. and cooled to 0° C. to 5° C. and then stirred for 4 hours. Filtered the precipitated product and washed with chilled water (100 ml) and then washed with chilled acetone (100 ml). To the resultant wet product charged water (900 ml), heated to 90° C. to 95° C. and stirred for 30 minutes at same temperature. Cooled to 25° C. to 30° C. and then to 0° C. to 5° C. and stirred for 4 hours. Filtered the product and washed with chilled water (50 ml) and then washed with chilled acetone (100 ml). The wet product was dried at 70° C. to 75° C. under reduced pressure to provide the title compound.

Yield: 90 gms.
HPLC purity: 98.5%.
HPA: Not detected.
The XRPD is set forth in FIG. 1.

Example 2

Preparation of Tenofovir (Using Sodium Hydride and Magnesium Chloride)

To a clean 3-necked 2 L round bottom flask equipped with a mechanical stirrer, thermometer socket and addition funnel was charged dimethyl formamide (500 ml) and 9-[2-(R)-(hydroxy)propyl]adenine of formula III (100 gms) at temperature 20° C. to 35° C. Cooled to 0° C. to 5° C. and added sodium hydride (41.5 gms) and stirred for 60 minutes at same temperature. Heated to 25° C. to 30° C. and added magnesium chloride (56 gms) and stirred for 2 hours at 25° C. to 30° C. To the reaction mass added diethyl p-toluene sulfonyloxy methyl phosphonate (225 gms) at 25° C. to 30° C. and stirred for 1 hour at same temperature. Heated to 70° C. to 75° C. and stirred for 4 hours at same temperature. Reaction was monitored by HPLC and observed 75% of the reaction product formed. Cooled the reaction temperature to 25° C. to 30° C. and added methanol (20 ml) and then solvent was removed from the reaction mixture by distillation under vacuum at below 70° C. to obtain (R)-9-[2-(diethylphosphono methoxy)propyl]adenine of formula II as thick residue. Cooled the resultant residue to 25° C. to 35° C. and charged aqueous hydrobromic acid (524 ml). Heated to 90° C. to 95° C. and stirred for 5 hours at same temperature. After completion of the reaction, the reaction mass was cooled to 25° C. to 30° C. and stirred for 30 minutes at same temperature. Filtered the salts formed and washed the salts with methylene chloride (300 ml). Taken filtrate and separated methylene chloride layer from the aqueous layer and then adjusted the aqueous layer pH to 2.5 to 3 with 50% sodium hydroxide solution at 20° C. to 30° C. Cooled the solution to 0° C. to 5° C. and stirred for 4 hours. Filtered the precipitated product and washed with chilled water (100 ml) and then washed with chilled acetone (100 ml). To the resultant wet product charged water (1200 ml), heated to 95° C. to 100° C. and stirred for 30 minutes at same temperature. Cooled to 25° C. to 30° C. and then to 0° C. to 5° C. and stirred for 4 hours. Filtered the product and washed with chilled water (50 ml) and then washed with chilled acetone (100 ml). The wet product was dried at 70° C. to 75° C. under reduced pressure to provide the title compound.
Yield: 85 gms.
HPLC purity: 98.7%.
HPA: Not detected.

Example 3

Preparation of Tenofovir (Using Sodium Amide and Magnesium Acetate)

To a clean 3-necked 2 L round bottom flask equipped with a mechanical stirrer, thermometer socket and addition funnel was charged dimethyl formamide (200 ml) and 9-[2-(R)-(hydroxy)propyl]adenine of formula III (50 gms) at temperature 20° C. to 35° C. Cooled to 0° C. to 5° C. and added sodium amide (20.2 gms) at temperature 0° C. to −10° C. and stirred for 30 minutes at same temperature. Heated to 25° C. to 30° C. and stirred for 2 hours at same temperature. Added magnesium acetate (36.8 gms) and stirred for 1 hour at 25° C. to 30° C. Heated to 60° C. to 65° C. and stirred for 2 hours at same temperature and then again heated to 75° C. to 80° C. At this temperature added diethyl p-toluene sulfonyloxy methyl phosphonate (125 gms) and stirred for 4 hours at same temperature. Reaction was monitored by HPLC and observed 55% of the product formed. The solvent was removed from the reaction mixture by distillation under vacuum at below 70° C. to obtain (R)-9-[2-(diethylphosphono methoxy)propyl]adenine of formula II as thick residue. Cooled the resultant residue to 25° C. to 35° C. and charged aqueous hydrobromic acid (330 ml). Heated to 90° C. to 95° C. and stirred for 2 hours at same temperature. After completion of the reaction, the reaction mass was cooled to 25° C. to 30° C. and stirred for 30 minutes at same temperature. Filtered the salts formed and washed the salts with methylene chloride (150 ml). Taken filtrate and separated methylene chloride layer from the aqueous layer and then adjusted the aqueous layer pH to 2.5 to 3 with 50% sodium hydroxide solution at 20° C. to 30° C. Stirred the solution for 1 hour at 20° C. to 25° C. and cooled to 0° C. to 5° C. and then stirred for 4 hours. Added acetone (100 ml) 0° C. to 5° C. and stirred for 2 hours. Filtered the precipitated product and washed with chilled water (50 ml) and then washed with chilled acetone (50 ml). To the resultant wet product charged water (175 ml), heated to 90° C. to 95° C. and stirred for 30 minutes at same temperature. Cooled to 25° C. to 30° C. and then to 0° C. to 5° C. and stirred for 4 hours. Filtered the product and washed with chilled water (25 ml) and then washed with chilled acetone (50 ml). The wet product was dried at 70° C. to 75° C. under reduced pressure to provide the title compound.
Yield: 38 gms.
HPLC purity: 97.5%

Example 4

Preparation of Tenofovir (Using n-butyl Magnesium Chloride)

To a clean 3-necked 2 L round bottom flask equipped with a mechanical stirrer, thermometer socket and addition funnel was charged tetrahydrofuran (100 ml) and 9-[2-(R)-(hydroxy)propyl]adenine of formula III (20 gms) at temperature 20° C. to 35° C. Cooled to 0° C. to 5° C. and added n-butyl magnesium chloride (78 ml, 2M solution in tetrahydrofuran). Stirred for 30 minutes at 0° C. to 5° C. and then heated to 25° C. to 30° C. and stirred for 2 hours at same temperature. Again temperature was heated to 65° C. to 70° C. and stirred for 1 hour at same temperature. At this temperature added diethyl p-toluene sulfonyloxy methyl phosphonate (45 gms) and stirred for 10 hours at same temperature. After completion of the reaction, the solvent was removed from the reaction mixture by distillation under vacuum at below 60° C. to obtain (R)-9-[2-(diethylphosphono methoxy)propyl]adenine of formula II as residue. Cooled the resultant residue to 25° C. to 35° C. and charged aqueous hydrobromic acid (130 ml). Heated to 90° C. to 95° C. and stirred for 2 hours at same temperature. After completion of the reaction, the reaction mass was cooled to 25° C. to 30° C. and stirred for 30 minutes at same temperature. Filtered the salts formed and washed the salts with methylene chloride (300 ml). Taken filtrate and separated methylene chloride layer from the aqueous layer and then adjusted the aqueous layer pH to 2.5 to 3 with 50% sodium hydroxide solution at 20° C. to 30° C. Stirred the solution for 1 hour at 20° C. to 25° C. and cooled to 0° C. to 5° C. and then stirred for 4 hours. Filtered the precipitated product and washed with chilled water (30 ml) and then washed with chilled acetone (30 ml). To the resultant wet product charged water (200 ml), heated to 90° C. to 95° C. and stirred for 30 minutes at same temperature. Cooled to 25° C. to 30° C. and then to 0° C. to 5° C. and stirred for 4 hours. Filtered the product and washed with chilled water (30 ml) and then washed with chilled acetone (300 ml). The wet product was dried at 70° C. to 75° C. under reduced pressure to provide the title compound.

Yield: 14 gms.

HPLC purity: 98.2%

Example 5

Preparation of Tenofovir Disoproxil Fumarate

To a clean 3-necked 1 L round bottom flask equipped with a mechanical stirrer, thermometer socket, addition funnel and dean-stark apparatus was charged cyclohexane (400 ml) and tenofovir (50 gms, obtained from example 1) and triethyl amine (34 gms) at temperature 20° C. to 35° C. Heated to 80° C. to 85° C. and stirred for 2 hours and simultaneously removed water liberated. After complete removal of water from the reaction, the solvent was removed completely from the reaction mixture by distillation under vacuum at below 65° C. and to the obtained residue, charged N-methyl pyrrolidinone (150 ml) and triethyl amine (34 gms) at 25° C. to 30° C. Heated to 50° C. to 55° C. and added chloromethyl isopropyl carbonate (125 gms) at same temperature and stirred for 4 hours. After completion of the reaction, the reaction mass was cooled to 20° C. to 25° C. and washed with cyclohexane (200 ml) and separated the product containing organic layer. To the organic layer charged methylene chloride (500 ml) and stirred for 1 hour at 10° C. to 15° C. Filtered the salts formed and washed the filtrate with water (500 ml), separated the layers and charged water (500 ml) to the organic layer. Adjusted pH to 6.5 to 7.5 with 10% ammonia solution and separated the organic layer from the aqueous layer. The solvent was removed from the organic layer under vacuum at below 35° C. to obtain oily product and then the oily product was diluted with isopropanol (150 ml).

In a clean another 3-necked 1 L round bottom flask equipped with a mechanical stirrer, thermometer socket and addition funnel was charged isopropanol (350 ml) and Fumaric acid (19 gms). Heated to 50° C. to 55° C. and stirred for 20 minutes and added above obtained oily product solution at 50° C. to 55° C. Stirred for 30 minutes at this temperature and cooled to 25° C. to 30° C. and stirred for 1 hour. Again cooled to 0° C. to 5° C. and stirred for 4 hours. Filtered the product and washed with chilled isopropanol (75 ml). The wet product was dried at 35° C. to 40° C. under reduced pressure to provide the title compound as crude (80 gms).

In another clean 3-necked 1 L round bottom flask equipped with a mechanical stirrer, thermometer socket and addition funnel was charged ethyl acetate (450 ml) and crude product (80 gms) at temperature 10° C. to 15° C. Stirred the slurry for 1 hour and filtered the product and washed with chilled ethyl acetate (50 ml). The wet product was dried at 35° C. to 40° C. for 6 hours under reduced pressure to provide the title compound.

Yield: 55 gms.

HPLC purity: 98.9%.

HPA: Not detected.

Figure 2:
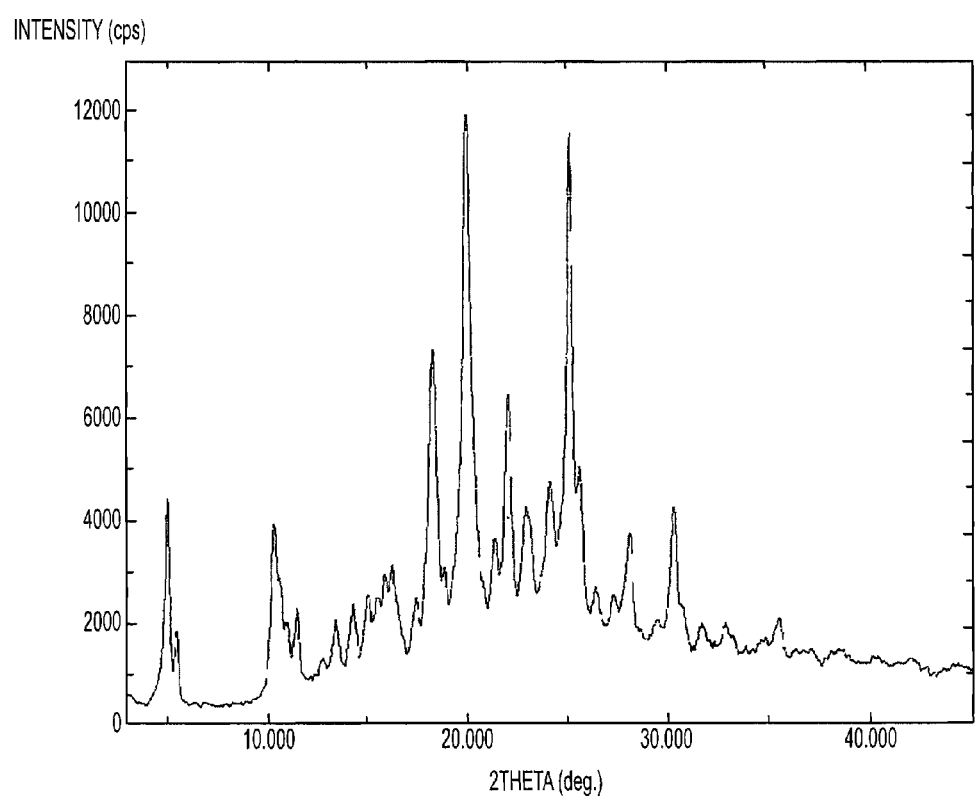
FIG. 2 is the characteristic powder X-ray diffraction pattern (XRPD) of tenofovir disoproxil fumarate.

The XRPD is set forth in FIG. 2.

Figure 3:
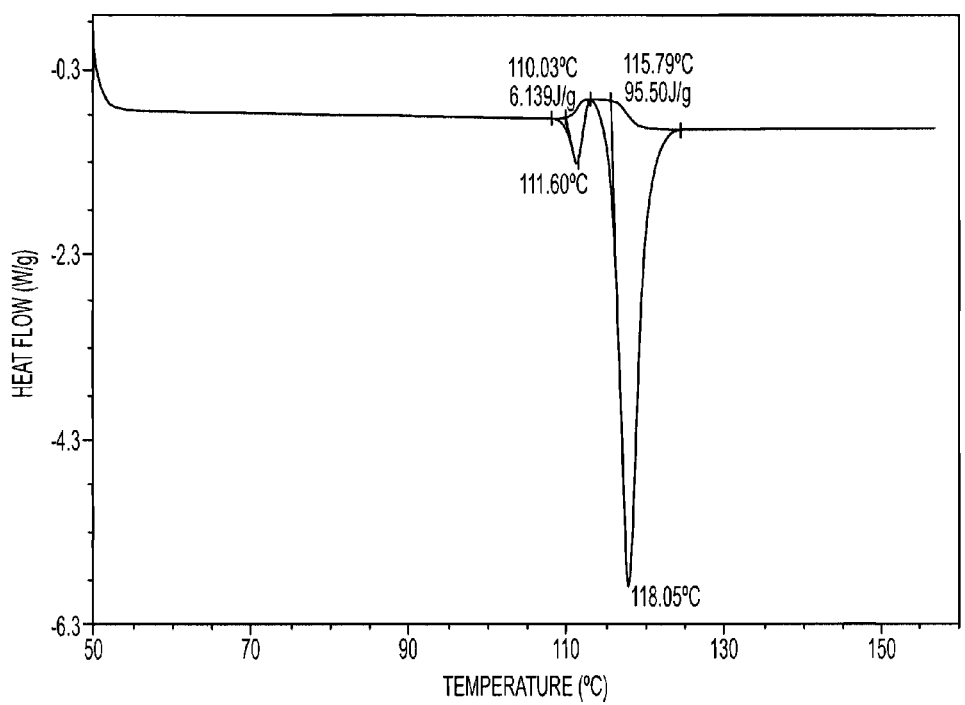
FIG. 3 is the characteristic differential scanning calorimetric (DSC) theremogram of tenofovir disoproxil fumarate.

The DSC is set forth in FIG. 3.

Residual solvents are shown in Table I:

TABLE I

| Solvent | Content (ppm) | Solvent | Content (ppm) |
| --- | --- | --- | --- |
| Acetone | below 5 | Toluene | below 3 |
| Isopropanol | 142 | Dimethyl formamide | below 40 |
| Ethyl acetate | below 3 | N-methyl pyrrolidinone | 92 |
| Dichloromethane | below 16 | Triethyl amine | below 16 |
| Cyclohexane | below 1 | | |

Example 6

Tenofovir was prepared from 9-[2-(R)-(hydroxy)propyl] adenine of formula III using sodium hydride as base without use of a metal salt, using a procedure analogous to that employed in Example 2, as described in the following Table II (results after 4 hours reaction, monitored by HPLC):

TABLE II

| HPA | Sodium hydride | Magnesium chloride | DESMP | tenofovir | HPA | Formula IV |
| --- | --- | --- | --- | --- | --- | --- |
| 10 gms | 2.5 gms | Nil | 25 gms | 15% | 25% | 12% |
| 10 gms | 5 gms | Nil | 20 gms | 40% | 13% | 12% |

Below are measurements using HPLC of three batches of tenofovir after 4 hours of the reaction monitoring by HPLC, prepared according to the process of the present invention is set forth below in Table III.

TABLE III

| Base | metal salt | tenofovir | HPA | Formula IV |
| --- | --- | --- | --- | --- |
| sodium amide | magnesium chloride | 78% | 3% | 4% |
| sodium hydride | magnesium chloride | 75% | 5% | 4% |
| sodium amide | magnesium acetate | 55% | 11% | 5% |

Table II shows that level of purity of tenofovir obtained from HPA, which use base such as sodium hydride or lithium hydride alone, other than combination of a base and a metal salt, in contrast to the process described herein, are higher conversion level of tenofovir from HPA, as shown in Table III.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the specification appended hereto.

We claim:
1. A process for the preparation of tenofovir of formula I, comprising the steps of:

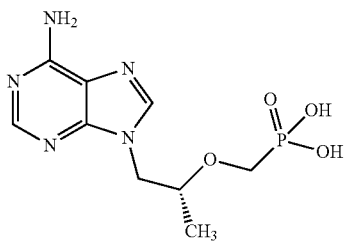

Formula I a) reacting 9-[2-(R)-(hydroxy)propyl]adenine (HPA) of formula III

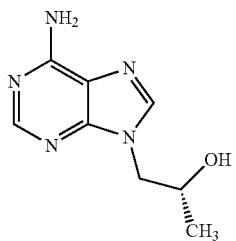

Formula III with di-Alk-p-toluene sulfonyloxy methyl phosphonate in presence of a base and a metal salt in an organic solvent to obtain (R)-9-[2-(di-Alk-phosphono methoxy)propyl]adenine of formula II;

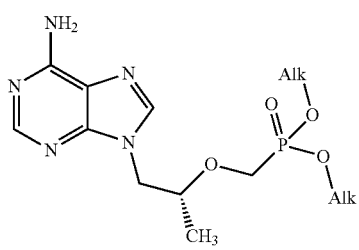

Formula II wherein "Alk" represents $C_{1-4}$ alkyl, and wherein the metal salt is represented by the formula $MX_2$, wherein M represents a divalent metal cation, and X represents halide, acetate, or trifluoromethane sulfonate; and b) dealkylating the compound of formula II with a suitable dealkylating agent to obtain tenofovir.

2. The process of claim 1, further comprising the step of converting the tenofovir into a tenofovir disoproxil or a pharmaceutically acceptable salt thereof.

3. The process of claim 1, wherein the $C_{1-4}$ alkyl is selected from the group consisting of methyl, ethyl, propyl, butyl, isopropyl, and isobutyl.

4. The process of claim 1, wherein the base is selected from the group consisting of alkali metal hydroxides, alkali metal hydrides, amide bases, alkali metal alkoxides, and alkyl lithium compounds.

5. The process of claim 1, wherein the divalent metal cation selected from the group consisting of zinc, beryllium, magnesium, calcium, strontium, and barium.

6. The process of claim 1, wherein the halide is selected from the group consisting of fluoro, bromo, chloro, and iodo.

7. The process of claim 1, wherein in the organic solvent is selected from the group consisting of amides, ethers, aromatic hydrocarbons, and nitriles.

8. The process of claim 1, wherein the organic solvent is selected from dimethyl formamide, dimethyl acetamide, dimethyl sulfoxide, N-methyl pyrrolidinone, toluene, tetrahydrofuran, acetonitrile, and mixtures thereof.

9. The process of claim 1, wherein the suitable dealkylating agent is selected from the group consisting of trialkyl silyl halides, hydrobromic acid, and methane sulfonic acid.

10. The process of claim 9, wherein the trialkyl silyl halides is selected from the group consisting of chloro trimethyl silane, bromotrimethyl silane, and iodo trimethyl silane.

11. A process for the preparation of tenofovir disoproxil fumarate, comprising the steps of:
a) reacting 9-[2-(R)-(hydroxy)propyl]adenine (HPA) with diethyl p-toluene sulfonyloxy methyl phosphonate in presence of a base selected from the group consisting of sodium amide and sodium hydride, and a metal salt selected from the group consisting of magnesium chloride and magnesium acetate, in an organic solvent, to obtain (R)-9-[2-(diethylphosphono methoxy)propyl]adenine;
b) dealkylating the (R)-9-[2-(diethylphosphono methoxy)propyl]adenine with aqueous hydrobromic acid to obtain tenofovir:
c) reacting the tenofovir with chloromethyl isopropyl carbonate to obtain tenofovir disoproxil; and
d) reacting of the tenofovir disoproxil with fumaric acid to obtain tenofovir disoproxil fumarate.

12. A process for the preparation of tenofovir of formula I, comprising the steps of:

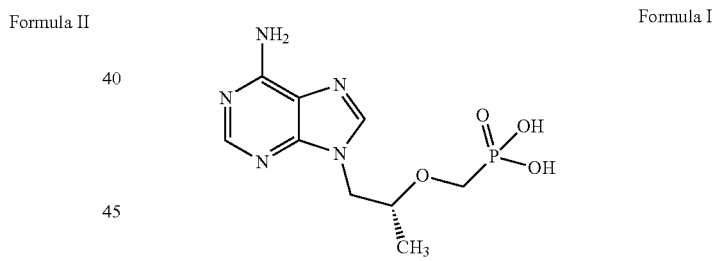

Formula I a) reacting 9-[2-(R)-(hydroxy)propyl]adenine (HPA) of formula III

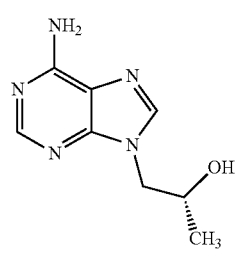

Formula III with di-Alk-p-toluene sulfonyloxy methyl phosphonate in presence of a base and a metal salt in an organic solvent to obtain (R)-9-[2-(di-Alk-phosphono methoxy)propyl]adenine of formula II;

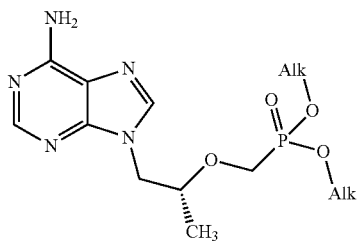

Formula II wherein "Alk" represents $C_{1-4}$ alkyl, and wherein the base is selected from the group consisting of sodium hydride, lithium hydride, sodium amide, potassium amide, sodium dimethyl amide, sodium methoxide, and butyl lithium; and b) dealkylating the compound of formula II a suitable dealkylating agent to obtain tenofovir.

13. The process of claim 12, further comprising the step of converting the tenofovir into a tenofovir disoproxil or a pharmaceutically acceptable salt thereof.

14. The process of claim 12, wherein the $C_{1-4}$ alkyl is selected from the group consisting of methyl, ethyl, propyl, butyl, isopropyl, and isobutyl.

15. The process of claim 12, wherein the organic solvent is selected from the group consisting of amides, ethers, aromatic hydrocarbons, and nitriles.

16. The process of claim 12, wherein the organic solvent is selected from dimethyl formamide, dimethyl acetamide, dimethyl sulfoxide, N-methylpyrrolidinone, toluene, tetrahydrofuran, acetonitrile, and mixtures thereof.

17. The process of claim 12, wherein the suitable dealkylating agent is selected from the group consisting of trialkyl silyl halides, hydrobromic acid, and methane sulfonic acid.

18. The process of claim 12, wherein the trialkyl silyl halides is selected from the group consisting of chloro trimethyl silane, bromotrimethyl silane, and iodo trimethyl silane.

* * * * *